(12) United States Patent
Gershon et al.

(10) Patent No.: US 10,076,475 B2
(45) Date of Patent: Sep. 18, 2018

(54) SHELL-STRUCTURED PARTICLES FOR SUNSCREEN APPLICATIONS

(71) Applicant: International Business Machines Corporation, Armonk, NY (US)

(72) Inventors: Talia S. Gershon, White Plains, NY (US); Yun Seog Lee, Yorktown Heights, NY (US); Ning Li, White Plains, NY (US); Devendra Sadana, Pleasantville, NY (US); Teodor K. Todorov, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/142,761

(22) Filed: Apr. 29, 2016

(65) Prior Publication Data

US 2017/0112728 A1    Apr. 27, 2017

Related U.S. Application Data

(60) Provisional application No. 62/245,277, filed on Oct. 23, 2015.

(51) Int. Cl.
*A61K 8/19* (2006.01)
*A61K 8/02* (2006.01)
(Continued)

(52) U.S. Cl.
CPC ............. *A61K 8/19* (2013.01); *A61K 8/025* (2013.01); *A61K 8/27* (2013.01); *A61Q 17/04* (2013.01);
(Continued)

(58) Field of Classification Search
CPC .......... A61K 2800/20; A61K 2800/621; A61K 2800/63; A61K 2800/651; A61K 8/19; A61K 8/27; A61Q 17/04
See application file for complete search history.

(56) References Cited

U.S. PATENT DOCUMENTS 3,761,261 A    9/1973   Ono et al.
3,863,007 A    1/1975   Warner, Jr.
(Continued)

FOREIGN PATENT DOCUMENTS

CN    103071535 A    5/2013
EP      1889810 A1   2/2008
(Continued)

OTHER PUBLICATIONS

Thokozane Moses Sithole, Synthesis and characterization of MBxOy:Eu (M=Ca, Sr, Ba) phosphors and TiO2 semiconductor for application in luminescence and energy materials, University of the Free State, Nov. 2014.
(Continued)

*Primary Examiner* — Rachael Eva Bredefeld
(74) *Attorney, Agent, or Firm* — Ryan, Mason & Lewis, LLP

(57) ABSTRACT

Shell-structured particles for sunscreen applications are provided herein. A method includes selecting one or more particles to serve as a core material in a sunscreen composition, wherein each of the one or more particles comprises a band gap within a predetermined range, and wherein said selecting is based on a desired absorption spectrum of the sunscreen composition; coating the one or more particles with at least one layer of zinc oxide. A composition includes selecting one or more particles to serve as a coating layer in a sunscreen composition, wherein each of the one or more particles comprises a band gap within a predetermined range, and wherein said selecting is based on a desired absorption spectrum of the sunscreen composition; and coating one or more zinc oxide particles with the one or more selected particles.

9 Claims, 2 Drawing Sheets

(51) Int. Cl.
  *A61K 8/27* (2006.01)
  *A61Q 17/04* (2006.01)
(52) U.S. Cl.
  CPC .... *A61K 2800/621* (2013.01); *A61K 2800/63* (2013.01); *A61K 2800/651* (2013.01)

(56) References Cited

U.S. PATENT DOCUMENTS

| | | |
|---|---|---|
| 4,549,195 A | 10/1985 | Bluzer |
| 5,011,782 A | 4/1991 | Lamb |
| 5,147,125 A | 9/1992 | Austin |
| 5,223,250 A * | 6/1993 | Mitchell ............ A61K 8/0241 424/401 |
| 5,441,726 A | 8/1995 | Mitchnick |
| 5,534,056 A | 7/1996 | Kuehnle |
| 5,553,630 A | 9/1996 | Dupuis et al. |
| 5,902,569 A | 5/1999 | Oshima |
| 6,419,909 B1 | 7/2002 | Lorant |
| 7,241,399 B2 | 7/2007 | Haubold |
| 9,056,063 B2 | 6/2015 | Hanson |
| 9,144,535 B1 | 9/2015 | Daly et al. |
| 9,144,536 B1 | 9/2015 | Daly et al. |
| 9,773,931 B2 | 9/2017 | Hossain |
| 2002/0122832 A1 | 9/2002 | Hanke |
| 2003/0102099 A1 | 6/2003 | Yadav |
| 2004/0209081 A1 | 10/2004 | Hagihara |
| 2005/0008861 A1 | 1/2005 | Yadav et al. |
| 2005/0048010 A1 | 3/2005 | Kliss |
| 2005/0208005 A1 | 9/2005 | Giroud |
| 2005/0227063 A1 | 10/2005 | Lawandy |
| 2005/0238600 A1 | 10/2005 | Lien |
| 2005/0265935 A1 | 12/2005 | Hollingsworth |
| 2006/0228310 A1 | 10/2006 | Lyth |
| 2006/0270053 A1 | 11/2006 | Tilak |
| 2007/0280895 A1 | 12/2007 | Weimer |
| 2008/0149850 A1 | 6/2008 | Tardif et al. |
| 2008/0220026 A1 | 9/2008 | Maltra |
| 2009/0022765 A1 | 1/2009 | Chung et al. |
| 2009/0104130 A1 | 4/2009 | Bernstein |
| 2009/0258072 A1 | 10/2009 | Schlossman |
| 2009/0258230 A1 | 10/2009 | Schlossman |
| 2010/0008872 A1 | 1/2010 | Katusic |
| 2010/0055138 A1 | 3/2010 | Margulies |
| 2011/0268678 A1 | 11/2011 | Armstrong |
| 2013/0216834 A1 | 8/2013 | Hashimoto |
| 2014/0142213 A1 | 5/2014 | Weiss |
| 2015/0283059 A1 | 10/2015 | Nagare |
| 2016/0082513 A1 | 3/2016 | Niedermeyer |

FOREIGN PATENT DOCUMENTS

| | | |
|---|---|---|
| JP | 09059591 A | 3/1997 |
| JP | 2008024677 A | 2/2008 |
| JP | 2011102291 A | 5/2011 |
| WO | 2005023535 A2 | 3/2005 |
| WO | 2008017176 A2 | 2/2008 |
| WO | 2008079758 A1 | 7/2008 |
| WO | 2011004133 A2 | 1/2011 |
| WO | 2012046204 A1 | 4/2012 |
| WO | 2013040149 | 3/2013 |
| WO | 2013094639 A1 | 6/2013 |
| WO | 2014049139 A1 | 4/2014 |
| WO | 2014077189 | 5/2014 |
| WO | 2016020168 A1 | 2/2016 |

OTHER PUBLICATIONS

Sardar et al., Optical-absorption intensities and intermanifold emission cross sections of trivalent erbium ions in calcium fluorophosphate, Journal of Applied Physics, Sep. 2005.
Lu et al., 2008—White Up-Conversion Luminescence in Rare-Earth-Ion-Doped YAlO3 Nanocrystals, J. Phys. Chem. C 2008, 112, 15071-15074.
Refractive index of ZnO (Zinc oxide)—Bond-o, http://refractiveindex.info/?shelf=main&book=ZnO&page=Bond-o, Mar. 25, 2016.
Refractive index of SiO2 (Silicon dioxide, Silica, Quartz)—Malitson, http://refractiveindex.info/?shelf=main&book=SiO2&page=Malitson, Mar. 25, 2016.
Schubert et al., Design of multilayer antireflection coatings made from co-sputtered and low-refractive-index materials by genetic algorithm. Optics Express vol. 16, No. 8, 2008.
Law et al., ZnO—Al2O3 and ZnO—TiO2 Core-Shell Nanowire Dye-Sensitized Solar Cells. J. Phys. Chem. B 2006, 110, 22652-22663.
Pu et al., Core/shell structured ZnO/SiO2 nanoparticles: Preparation, characterization and photocatalytic property. Applied Surface Science 257 (2010) 393-397.
Mantz et al., Progress in Organic Coatings 47 (2003) 432-442, "A multiple-scattering model analysis of zinc oxide pigment for spacecraft thermal control coatings."
Song et al., Toxicology Letters 199 (2010) 389-397, "Role of the dissolved zinc io and reactive oxygen species in cytotoxicity of ZnO nanoparticles."
Bohren et al., "Absorption and Scattering of Light by Small Particles", Wiley-VCH, © 2004, Weinheim.
Bae et al., J. Phys. Chem. B 2005, 109, 2526-2531, "Comparative Structure and Optical Properties of Ga-, In-, and Sn-Doped ZnO Nanowires Synthesized by thermal evaporation."
NanoComposix, Silver Nanoparticles: Optical Properties, http://nanocomposix.com/pages/silver-nanoparticles-optical-properties, Apr. 20, 2016.
Awazu et al., 2007—A Plasmonic Photocatalyst Consisting of Silver Nanoparticles Embedded in Titanium Dioxide, J. Am. Chem. Soc. 2008, 130, 1676-1680.
Sherry et al., Localized Surface Plasmon Resonance Spectroscopy of Single Silver Nanocubes, Nano Lett., vol. 5, No. 10, 2005.
Aguirre et al., Ag@ZnO Core_Shell Nanoparticles Formed by the Timely Reduction of Ag+ Ions and Zinc Acetate Hydrolysis in N,N-Dimethylformamide: Mechanism of Growth and Photocatalytic Properties, J. Phys. Chem. C 2011, 115, 24967-24974.
Haynes et al., Nanosphere Lithography: Tunable Localized Surface Plasmon Resonance Spectra of Silver Nanoparticles, J. Phys. Chem. B 2000, 104, 10549-10556.
U. Nobbmann, "FAQ: How important are refractive index & adsorption for nanoparticles?" http://www.materials-talks.com/blog/2014/08/05/faq-how-important-are-refractive-index-absorption-for-nanoparticles/ Materials Talks, Aug. 5, 2014, p. 1-2.
Tsuzuki et al., Nanoparticle Coatings for UV Protective Textiles, RJTA vol. 14 No. 2 2010.
Li et al., Transparent and Light-Emitting Epoxy Super-Nanocomposites Containing ZnO-QDs/SiO2 Nanocomposite Particles as Encapsulating Materials for Solid-State Lighting, J. Phys. Chem. C 2008, 112, 18616-18622.
Li et al., 2011—Sol-gel preparation and characterization of nanoporous ZnO_SiO2 coatings with broadband antireflection properties, Applied Surface Science 257 (2011) 9752-9756.
Messaoudi et al., "Synthesis and characterization of ZnO/Cu2O core-shell nanowires grown by two-step electrodeposition method." Applied Surface Science 343 (2015) 148-152.
Luo et al., Facile synthesis of composition-tuned ZnO/ZnxCd1-xSe nanowires for photovoltaic applications, Nanoscale Research Letters (2015) 10:181.
Smijs et al. Titanium Dioxide and Zinc Oxide Nanoparticles in Sunscreens: Focus on Their Safety and Effectiveness, Nanotechnology, Science and Applications 4:95-112, Oct. 2011.
Wikipedia, List of Refractive Indices, last modified Feb. 15, 2017; https://en.wikipedia.org/wiki/List_of_refractive_indices.
Naylor et al. "Sunscreens," accessed 2017, http://telemedicine.org/sundam/sundam2.4.2.html.
Machine translation WO 2011/004133, printed 2017.
Wikipedia "Band Gap" last modified Jul. 18, 2017, https://en.wikipedia.org/wiki/Band_gap.
Machine translation WO 2012/046204, printed 2017.
Simon Aldridge and Anthony Downs. The Group 13 Metals Aluminum, Gallium, Indium and Thallium Chemical Patterns and Peculiarities, 2011 John Wiley & Sons, Ltd., p. 623 (Year: 2011).

(56) References Cited

OTHER PUBLICATIONS

Family Health Team, "Best Ways to Protect Your Hair From Sun Damage," Cleveland Clinic, health essentials, <https://health.clevelandclinic.org/2014/06/best-ways-to-protect-your-hair-from-sun-damage/>, published Aug. 22, 2014, p. 1-4.
Cuprous Oxide, Chemical Book, pp. 1-4, Accessed Sep. 18, 2017, https://www.chemicalbook.com/ProductChemicalPropertiesCB9853041_EN.htm.
Ultraviolet Radiation and the Intersun Programme [online]. WHO, Nov. 2003 [retrieved on Jun. 8, 2017]. Retrieved from the internet <http://www.whoint/uv/uv_and_health/en/>.
Faure, B. et al. Dispersion and Surface Functionalization of Oxide Nanoparticles for Transparent Photocatalytic and UV-protecting Coatings and Sunscreens, Sci Technol. Adv. Mater 14 2013, 023001.
Tariq Jan, et al. Sn Doping Induced Enhancement in the Activity of ZnO Nanostructures Against Antibiotic Resistant *S. aureus* Bacteria; Int J. Nanomedicine, vol. 8, pp. 3679-3687; Published online Sep. 30, 2013.
Bhatti et al. Optical Properties of Chromium & Cobalt Doped Zinc Oxide Powder Prepared by Sol-Gel Combustion Method, with the Assistance of Microwave Radiations; International Journal of Advanced Tech. in Engineering and Science; vol. 3, Issue 10; pp. 80-85; published Oct. 2015.
English language translation of WO 2013 094639 (A1) (Year 2013).
Machine translation, JP 2008-024677, printer 2018.
Kelly et al. "The Optical Properties of Metal Nanoparticles: The Influence of Size, Shape and Dielectric Environment," Journal of Physical Chemistry B 107:668-677, 2003.
Garcia, "Surface Plasmons in Metallic Nanoparticles: Fundamentals and Applications," Journal of Physics D: Applied Physics 44(28), 283001, 2011.

\* cited by examiner

SHELL-STRUCTURED PARTICLES FOR SUNSCREEN APPLICATIONS

FIELD

The present application generally relates to chemical technology, and, more particularly, to sunscreen technologies.

BACKGROUND

Sunscreen creams and other such compositions are commonly used to prevent ultraviolet (UV) radiation (also referred to herein as "light" in this context) from reaching the skin of a human user and causing damage. It is noted that UV light is an electromagnetic radiation with a wavelength range between approximately 280 nanometers (nm) and approximately 400 nanometers (specifically, that is the range of UV radiation that is not absorbed by the ozone).

A common active ingredient of existing sunscreen compositions is zinc oxide (ZnO). ZnO is a semiconductor that has a specific band gap, and particles of ZnO used in existing sunscreen compositions are typically approximately 50-300 nm in size. Additionally, in existing sunscreen compositions, typical ZnO materials are capable of absorbing UV light (that is, blocking the UV light from passing through the sunscreen composition to be absorbed by the skin of the user) within a wavelength range of approximately 290 nm through only approximately 350-380 nm.

Additionally, high sun protection factor (SPF) sunscreen compositions, which can absorb a large majority of the UV light in the range of 290-380 nm, require the addition of a higher density of ZnO particles, which causes the composition to become white and/or opaque due to light scattering from the ZnO particles, and which is an often undesirable property to consumers.

SUMMARY

In one embodiment of the present invention, oxide-based nanoparticles for use in sunscreen applications are provided. An exemplary method can include selecting one or more particles to serve as a core material in a sunscreen composition, wherein each of the one or more particles comprises a band gap within a predetermined range, and wherein said selecting is based on a desired absorption spectrum of the sunscreen composition; coating the one or more particles with at least one layer of zinc oxide.

In another embodiment of the invention, a sunscreen composition can include one or more particles constituting a core material in a sunscreen composition, wherein each of the one or more particles comprises a band gap within a predetermined range, and wherein said one or more particles are selected based on a desired absorption spectrum of the sunscreen composition; and at least one layer of zinc oxide particles coating the one or more selected particles.

Additionally, in one embodiment of the present invention, an exemplary method can include selecting one or more particles to serve as a coating layer in a sunscreen composition, wherein each of the one or more particles comprises a band gap within a predetermined range, and wherein said selecting is based on a desired absorption spectrum of the sunscreen composition; and coating one or more zinc oxide particles with the one or more selected particles.

In yet another embodiment of the invention, a sunscreen composition can include one or more zinc oxide particles constituting a core material in a sunscreen composition; and one or more particles coating the one or more zinc oxide particles, wherein each of the one or more particles comprises a band gap within a predetermined range, and wherein said one or more particles are selected based on a desired absorption spectrum of the sunscreen composition.

These and other objects, features and advantages of the present invention will become apparent from the following detailed description of illustrative embodiments thereof, which is to be read in connection with the accompanying drawings.

DETAILED DESCRIPTION

Figure 1A:
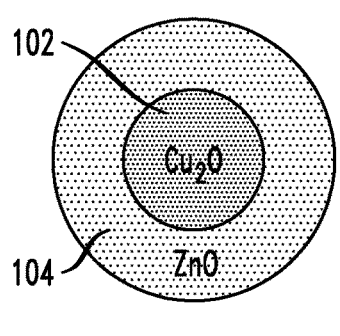
FIG. 1A is a diagram illustrating a core-shell structure, according to an exemplary embodiment of the invention.

As described herein, an embodiment of the present invention includes shell-structured particles for sunscreen applications. As further detailed herein, one or more embodiments of the invention include generating compositions and methods of use thereof for effectively blocking more and/or all of the complete spectrum of UV light (that is, as noted above, the UV radiation that is not absorbed by the ozone, and which ranges between approximately 280 nm and 400 nm) while also preventing whitening effects caused by the scattering of light in the visible spectrum (that is, radiation between approximately 400 nm and 700 nm).

At least one embodiment of the invention includes introducing a copper oxide ($Cu_2O$) particle or coating layer to form a ZnO—$Cu_2O$ or $Cu_2O$—ZnO core-shell structure particle for use in sunscreen compositions. As detailed herein, utilization of $Cu_2O$ (and/or analogous materials) can provide extended optical absorption (for sunscreen compositions) of wavelengths of light up to approximately 500 nm. The degree and/or the range of such extended absorption can be controlled by the size of the $Cu_2O$ particle, the thickness of the $Cu_2O$ coating, and/or the volume ratio between ZnO and $Cu_2O$.

As noted, in at least one embodiment of the invention, the $Cu_2O$ material can be replaced with one or more other materials having a band gap of approximately 2-3 electron volts (eV), such as, for example, zinc oxy-sulfide (ZnOS), $ZnO_xS_{1-x}$, wherein $0 \leq x \leq 1$, indium sulfide ($In_2S_3$), indium oxy-sulfide ($In_2(O_xS_{y1-x})_3$), wherein $0 \leq x \leq 1$, or combinations thereof. Such materials can be utilized, alone or in combination, to tune the absorption spectrum of the sunscreen composition.

In one or more embodiments of the invention, the core portion of a core-shell structure can include a single particle or multiple particles. Additionally, in at least one embodiment of the invention, the surface of the core-shell structure can be roughened to provide reduced optical reflection.

Further, as detailed herein, one or more embodiments of the invention can include applying an ARC to the outside and/or exterior surface of the core-shell particles to minimize reflection from the particles. In such an embodiment, the ARC can include any material having a refractive index between that of ZnO (or $Cu_2O$) and air (or surrounding media), which allows light to better couple into the core-shell particle structure and limits and/or prevents scattering at the ZnO ($Cu_2O$) interface. Such materials can include, for example, silicon dioxide ($SiO_2$), magnesium fluoride ($MgF_2$), fluoropolymers, etc.

Additionally, in such an embodiment, the ARC can include a single layer or can be comprised of multiple layers, wherein the refractive index of the layers are graded between that of the ZnO (or $Cu_2O$) and that of the surrounding media (such as air). Further, an ARC utilized in one or more embodiments of the invention can be dense or porous, wherein porous layers can contain an effective refractive index between that of air and that of the coating and/or shell material. Additionally, an ARC utilized in one or more embodiments of the invention can be smooth or roughened, wherein roughened layers can contain an effective refractive index between that of air and that of the coating and/or shell material.

Figure 1B:
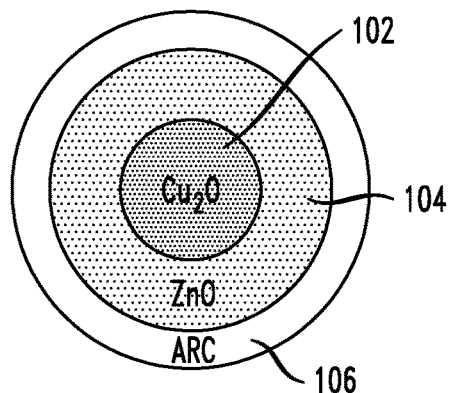
FIG. 1B is a diagram illustrating a core-shell structure with an anti-reflective coating (ARC), according to an exemplary embodiment of the invention.

FIG. 1A is a diagram illustrating a core-shell structure, according to an exemplary embodiment of the invention. Specifically, FIG. 1A depicts a $Cu_2O$ core 102 coated by a ZnO shell 104. Additionally, FIG. 1B is a diagram illustrating a core-shell structure with an ARC, according to an exemplary embodiment of the invention. Specifically, FIG. 1B depicts a $Cu_2O$ core 102 coated by a ZnO shell 104, and the core-shell structure further coated by an ARC layer 106 (such as, for example, $SiO_2$).

Figure 2A:
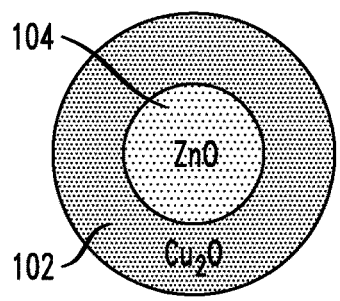
FIG. 2A is a diagram illustrating a core-shell structure, according to an exemplary embodiment of the invention.
Figure 2B:
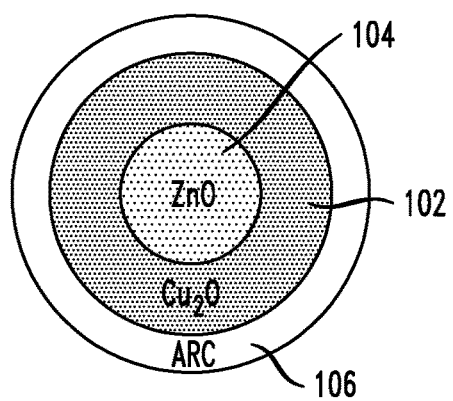
FIG. 2B is a diagram illustrating a core-shell structure with an ARC, according to an exemplary embodiment of the invention.

FIG. 2A is a diagram illustrating a core-shell structure, according to an exemplary embodiment of the invention. Specifically, FIG. 2A depicts a ZnO core 104 coated by a $Cu_2O$ shell 102. Additionally, FIG. 2B is a diagram illustrating a core-shell structure with an ARC, according to an exemplary embodiment of the invention. Specifically, FIG. 2B depicts a ZnO core 104 coated by a $Cu_2O$ shell 102, and the core-shell structure further coated by an ARC layer 106 (such as, for example, $SiO_2$).

Figure 3:
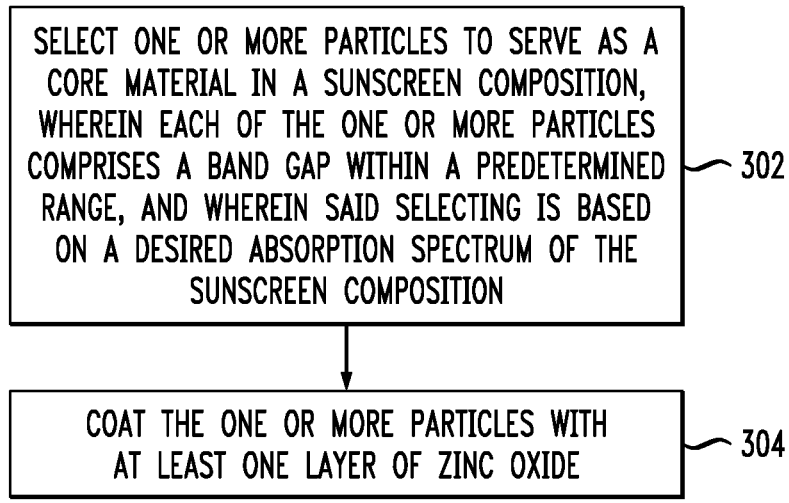
FIG. 3 is a flow diagram illustrating techniques according to an embodiment of the invention.

FIG. 3 is a flow diagram illustrating techniques, according to an embodiment of the present invention. Step 302 includes selecting one or more particles to serve as a core material in a sunscreen composition, wherein each of the one or more particles comprises a band gap within a predetermined range (for example, between approximately two and three eV), and wherein said selecting is based on a desired absorption spectrum of the sunscreen composition. The one or more particles can include one or more copper oxide particles. Step 304 includes coating the one or more particles with at least one layer of zinc oxide.

The techniques depicted in FIG. 3 can also include adjusting the desired absorption spectrum of the sunscreen composition by adjusting the size of the one or more selected particles, adjusting the thickness of the at least one layer of zinc oxide coating the one or more particles, and/or adjusting the volume ratio between the one or more particles and the at least one layer of zinc oxide.

Additionally, the techniques depicted in FIG. 3 can include manipulating the surface of the at least one layer of zinc oxide coating the one or more particles to form a roughened surface. Further, at least one embodiment of the invention can include applying an anti-reflective coating to the surface of the at least one layer of zinc oxide, wherein the anti-reflective coating comprises a material having a refractive index within a predetermined range.

Also, an additional embodiment of the invention includes a composition that includes one or more particles constituting a core material in a sunscreen composition, wherein each of the one or more particles comprises a band gap within a predetermined range, and wherein said one or more particles are selected based on a desired absorption spectrum of the sunscreen composition; and at least one layer of zinc oxide particles coating the one or more selected particles. Such a composition can also optionally include an anti-reflective coating applied to the surface of the at least one layer of zinc oxide, wherein the anti-reflective coating comprises a material having a refractive index within a predetermined range.

Figure 4:
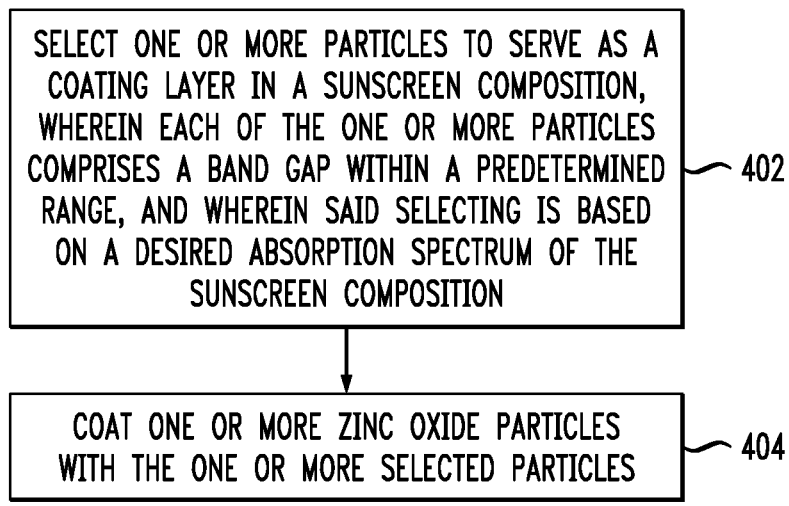
FIG. 4 is a flow diagram illustrating techniques according to an embodiment of the invention.

FIG. 4 is a flow diagram illustrating techniques, according to an embodiment of the present invention. Step 402 includes selecting one or more particles to serve as a coating layer in a sunscreen composition, wherein each of the one or more particles comprises a band gap within a predetermined range (for example, between approximately two and three eV), and wherein said selecting is based on a desired absorption spectrum of the sunscreen composition. The one or more selected particles can include one or more copper oxide particles. Step 404 includes coating one or more zinc oxide particles with the one or more selected particles.

The techniques depicted in FIG. 4 can also include adjusting the desired absorption spectrum of the sunscreen composition by adjusting the size of the one or more selected particles, adjusting the thickness of the one or more particles coating the one or more zinc oxide particles, and/or adjusting the volume ratio between the one or more selected particles and the one or more zinc oxide particles.

Additionally, the techniques depicted in FIG. 4 can include manipulating the surface of the one or more particles coating the one or more zinc oxide particles to form a roughened surface. Further, at least one embodiment of the invention can include applying an anti-reflective coating to the surface of the one or more particles coating the one or more zinc oxide particles, wherein the anti-reflective coating comprises a material having a refractive index within a predetermined range.

Further, yet another embodiment of the invention includes a composition that includes one or more zinc oxide particles constituting a core material in a sunscreen composition; and one or more particles coating the one or more zinc oxide particles, wherein each of the one or more particles comprises a band gap within a predetermined range, and wherein said one or more particles are selected based on a desired absorption spectrum of the sunscreen composition. Such a composition can also include an anti-reflective coating applied to the surface of the one or more particles coating the one or more zinc oxide particles, wherein the anti-reflective coating comprises a material having a refractive index within a predetermined range.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of another feature, step, operation, element, component, and/or group thereof.

At least one embodiment of the present invention may provide a beneficial effect such as, for example, generating extended optical absorption of wavelengths of light up to approximately 500 nm.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A sunscreen composition comprising:
one or more particles in a sunscreen composition, wherein each of the one or more particles comprises zinc oxy-sulfide and has a band gap between two electron volts and three electron volts, and wherein at least one layer of zinc oxide particles coats the one or more particles.

2. The composition of claim 1, further comprising:
an anti-reflective coating applied to the surface of that at least one layer of the zinc oxide particles.

3. The composition of claim 2, wherein the anti-reflective coating comprises silicon dioxide.

4. The composition of claim 2, wherein the anti-reflective coating comprises magnesium fluoride.

5. The composition of claim 2, wherein the anti-reflective coating comprises one or more fluoropolymers.

6. The composition of claim 2, wherein the anti-reflective coating comprises a single layer.

7. The composition of claim 2, wherein the anti-reflective coating comprises multiple layers.

8. The composition of claim 2, wherein the anti-reflective coating comprises one or more smooth layers.

9. The composition of claim 2, wherein the anti-reflective coating comprises one or more roughened layers.

* * * * *